US008987397B2

(12) United States Patent  
Kaneumi

(10) Patent No.: US 8,987,397 B2  
(45) Date of Patent: Mar. 24, 2015

(54) FLUORINE-CONTAINING COPOLYMER

(75) Inventor: Yoshiyama Kaneumi, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 13/822,721

(22) PCT Filed: Sep. 7, 2011

(86) PCT No.: PCT/JP2011/070344  
§ 371 (c)(1),  
(2), (4) Date: Mar. 13, 2013

(87) PCT Pub. No.: WO2012/036036  
PCT Pub. Date: Mar. 22, 2012

(65) Prior Publication Data  
US 2013/0172502 A1 Jul. 4, 2013

(30) Foreign Application Priority Data  
Sep. 13, 2010 (JP) ................. 2010-204430

(51) Int. Cl.  
C08F 230/08 (2006.01)  
A61K 8/891 (2006.01)  
A61Q 19/00 (2006.01)  
C08F 14/18 (2006.01)  
C08F 220/24 (2006.01)  
C08F 290/04 (2006.01)  
C08F 290/06 (2006.01)  
C09C 1/04 (2006.01)  
C09C 1/24 (2006.01)  
C09C 1/36 (2006.01)  
C09C 1/40 (2006.01)  
C09C 1/42 (2006.01)  
C09C 3/12 (2006.01)

(52) U.S. Cl.  
CPC ............. *C08F 14/185* (2013.01); *A61K 8/891* (2013.01); *A61K 2800/43* (2013.01); *A61Q 19/00* (2013.01); *C08F 220/24* (2013.01); *C08F 230/08* (2013.01); *C08F 290/04* (2013.01); *C08F 290/068* (2013.01); *C09C 1/043* (2013.01); *C09C 1/24* (2013.01); *C09C 1/3684* (2013.01); *C09C 1/405* (2013.01); *C09C 1/42* (2013.01); *C09C 3/12* (2013.01)  
USPC .......................................... 526/245; 524/261

(58) Field of Classification Search  
USPC ............................................ 526/245; 524/261  
See application file for complete search history.

(56) References Cited

U.S. PATENT DOCUMENTS

2008/0202384 A1* 8/2008 Peng et al. ............... 106/287.22  
2009/0080073 A1* 3/2009 Irita et al. ........................ 359/485  
2010/0101723 A1* 4/2010 Okamoto et al. ............ 156/306.6  
2010/0104879 A1* 4/2010 Okano ............................ 428/447

FOREIGN PATENT DOCUMENTS

| CN | 1927894 A | 3/2007 |
|---|---|---|
| CN | 101794075 A | 8/2010 |
| JP | 52-036588 | 3/1977 |
| JP | 52-039587 | 3/1977 |
| JP | 55-133490 | 10/1980 |
| JP | 58-180597 | 10/1983 |
| JP | 59-166596 | 9/1984 |
| JP | 60-190309 | 9/1985 |
| JP | 60-193615 | 10/1985 |
| JP | 61-289009 | 12/1986 |
| JP | 2010-521541 A | 6/2010 |
| WO | WO 2007/105633 A1 | 9/2007 |
| WO | WO 2008-106209 A2 | 9/2008 |
| WO | WO-2008/106209 A2 * | 9/2008 |
| WO | WO 2009/034773 A1 | 3/2009 |
| WO | WO-2009/034773 A1 * | 3/2009 |
| WO | WO 2010/101091 A1 | 9/2010 |
| WO | WO-2010/101091 A1 * | 9/2010 |

OTHER PUBLICATIONS

International Search Report from corresponding PCT application No. PCT/JP2011/070344 dated Dec. 13, 2011 (2 pgs).  
International Preliminary Report on Patentability and Written Opinion from corresponding PCT application No. PCT/JP2011/070344 dated Apr. 18, 2013 (5 pgs).

* cited by examiner

*Primary Examiner* — Peter D. Mulcahy  
*Assistant Examiner* — Henry Hu  
(74) *Attorney, Agent, or Firm* — Brinks Gilson & Lione

(57) ABSTRACT

Disclosed is a fluorine-containing copolymer comprising a copolymer of a polyfluoroalkyl alcohol(meth)acrylic acid derivative represented by the general formula:

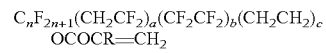

(R: a hydrogen atom or a methyl group, n: an integer of 1 to 6, a: an integer of 1 to 4, b: an integer of 1 to 3, c: an integer of 1 to 3) and a polysiloxane containing a terminal (meth)acryloyloxy group represented by the general formula:

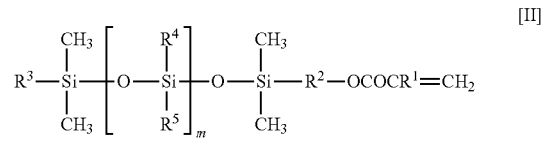

($R^1$: a hydrogen atom or a methyl group, $R^2$: a $C_1$-$C_6$ linear or branched divalent alkylene group, $R^3$: a $C_1$-$C_{30}$ linear or branched alkyl group, $R^4$ and $R^5$: a hydrogen atom, a methyl group, or a phenyl group, m: an integer of 1 to 200).

12 Claims, No Drawings

FLUORINE-CONTAINING COPOLYMER

RELATED APPLICATION

This application is a 35 U.S.C. §371 national phase filing of International Patent Application No. PCT/JP2011/070344, filed Sep. 7, 2011, through which and to which priority is claimed under 35 U.S.C. §119 to Japanese Patent Application No. 2010-204430, filed Sep. 13, 2010.

TECHNICAL FIELD

The present invention relates to a fluorine-containing copolymer. More particularly, the present invention relates to a fluorine-containing copolymer that can be effectively used as a surface-treatment agent for powder, etc.

BACKGROUND ART

The present applicant has previously proposed a fluorine-containing polymer comprising, as a polymerization unit, 5 to 100 wt. % of a polyfluoroalkyl alcohol(meth)acrylic acid derivative represented by the general formula:

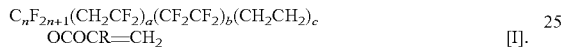

$$C_nF_{2n+1}(CH_2CF_2)_a(CF_2CF_2)_b(CH_2CH_2)_c OCOCR=CH_2 \quad [I]$$

An organic solvent solution or aqueous dispersion of this fluorine-containing copolymer can be effectively used as, for example, a surface modifier, such as a water- and oil-repellent or an oil barrier (see Patent Document 1).

Moreover, fluorine-based oils, such as perfluoropolyether oils, are increasingly used in combination with non-fluorine-based oils, such as hydrocarbon oils and silicone oils. However, since fluorine-based oils have a poor affinity for non-fluorine-based oils, which have been commonly used, it is very difficult at present to use them in combination.

It is also known that a polyfluoroalkyl(meth)acrylate copolymer is used as a film-forming component. For example, Patent Document 2 discloses a cosmetic comprising a copolymer of long-chain alkyl(meth)acrylate and fluorinated alkyl group-containing (meth)acrylate as a film-forming component. However, this copolymer has a softening point higher than room temperature, and film cracking and the like will occur under room temperature conditions.

Incidentally, it is reported that telomer compounds containing a perfluoroalkyl group having 8 to 12 carbon atoms are biologically degraded in the environment and converted to compounds having relatively high bioaccumulation and environmental concentration, causing concerns for exposure during treatment processes, and for release or diffusion from waste, treated substrates, etc., into the environment. Moreover, compounds containing a perfluoroalkyl group having 14 or more carbon atoms are very difficult to handle because of their physical and chemical properties. Hence, such compounds are rarely used in practice.

Furthermore, as for telomer compounds containing a perfluoroalkyl group having 8 or more carbon atoms (see Patent Documents 3 to 9), generation and incorporation of perfluorooctanoic acids with high bioaccumulation potential cannot be avoided in the production process of the telomer compounds. For these reasons, companies that produce such telomer compounds have retreated from the production of the compounds or promoted the use of alternative compounds containing a perfluoroalkyl group having 6 or less carbon atoms (see, for example, Patent Document 10).

However, compounds containing a perfluoroalkyl group having 6 or less carbon atoms cause a significant decrease in orientation on the surface of a treated substrate, and the melting point, glass transition point (Tg), etc., of the compounds are markedly lower than those of $C_8$ compounds. Accordingly, the compounds are highly influenced by their environmental conditions, such as temperature, humidity, stress, and contact with organic solvents. Consequently, the desired performance cannot be sufficiently achieved, and durability and other properties are affected.

PRIOR ART DOCUMENT

Patent Document

Patent Document 1 : WO 2009/034773 A1
Patent Document 2 : JP-B-3-46444
Patent Document 3 : JP-B-53-23270
Patent Document 4 : JP-B-53-23271
Patent Document 5 : JP-B-57-48035
Patent Document 6 : JP-B-2-45572
Patent Document 7 : JP-B-3-78244
Patent Document 8 : JP-B-4-4923
Patent Document 9: JP-B-4-11366
Patent Document 10 : WO 2007/105633 A1

OUTLINE OF THE INVENTION

Problem to be Solved by the Invention

An object of the present invention is to provide a fluorine-containing copolymer that is a copolymer of a polyfluoroalkyl alcohol (meth)acrylic acid derivative comprising a compound containing perfluoroalkyl group having 6 or less carbon atoms, which is said to have low bioaccumulation potential, and that has excellent water- and oil-repellency, water resistance, and affinity for pigments, etc.

Means for Solving the Problem

The present invention provides a fluorine-containing copolymer comprising a copolymer of a polyfluoroalkyl alcohol(meth)acrylic acid derivative represented by the general formula:

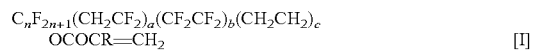

$$C_nF_{2n+1}(CH_2CF_2)_a(CF_2CF_2)_b(CH_2CH_2)_c OCOCR=CH_2 \quad [I]$$

wherein R is a hydrogen atom or a methyl group, n is an integer of 1 to 6, a is an integer of 1 to 4, b is an integer of 1 to 3, and c is an integer of 1 to 3, and a polysiloxane containing a terminal (meth)acryloyloxy group represented by the general formula:

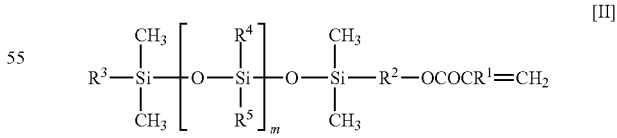

wherein $R^1$ is a hydrogen atom or a methyl group, $R^2$ is a $C_1$-$C_6$ linear or branched divalent alkylene group, $R^3$ is a $C_1$-$C_{30}$ linear or branched alkyl group, $R^4$ and $R^5$ are each a hydrogen atom, a methyl group, or a phenyl group, and m is an integer of 1 to 200. As used herein, the term "(meth)acrylic acid" refers to acrylic acid or methacrylic acid, and the term "(meth)acryloyloxy group" refers to an acryloyloxy group or a methacryloyloxy group.

Effect of the Invention

When the fluorine-containing copolymer of the present invention is released into the environment, the polyfluoroalkyl alcohol(meth)acrylic acid derivative [I], which is a monomer of the fluorine-containing copolymer, undergoes HF-elimination in the —$CH_2CF_2$— bonding site of the molecule, and a double bond is formed. The result is then subjected to ozone decomposition, etc., to have a structure that is easily decomposed into a compound with low environmental concentration and low bioaccumulation potential. Moreover, the fluorine-containing copolymer does not produce environmental loading substances (e.g., perfluoroalkyl carboxylic acids having 8 or more carbon atoms) in the production process thereof.

Furthermore, as a result of the copolymerization of the polyfluoroalkyl alcohol(meth)acrylic acid derivative [I] and the polysiloxane containing a terminal (meth)acryloyloxy group [II], the obtained fluorine-containing copolymer has excellent water- and oil-repellent performance, etc., as well as improved water resistance and affinity for pigments.

EMBODIMENTS FOR CARRYING OUT THE INVENTION

Examples of the polyfluoroalkyl alcohol(meth)acrylic acid derivative [I] include the following compounds, as described in Patent Document 1, and their corresponding methacrylic acid derivatives.

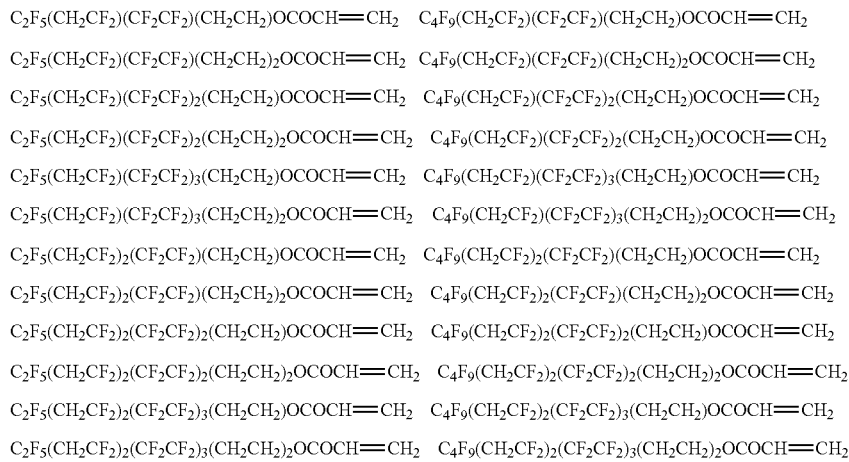

Moreover, examples of the polysiloxane containing a terminal (meth)acryloyloxy group [II] to be copolymerized with the polyfluoroalkyl alcohol(meth)acrylic acid derivative [I] include a polysiloxane comprising a siloxane bond as a main chain, such as dimethylpolysiloxane in which all of the side chains have methyl groups, methylphenylpolysiloxane in which some side chains have phenyl groups, or methylhydrogenpolysiloxane in which a part of the side chains has a hydrogen atom. Preferably, silicone oils containing a main chain of dimethylpolysiloxane are used. Moreover, $R^2$ is, for example, a $C_1$-$C_6$ linear or branched divalent alkylene group, such as methylene, ethylene, propylene, isobutylene, or hexylene. Such a group is derived from the ester group of (meth)acrylic acid ester.

Practically, commercial products, such as X-22-2426, X-22-174DX, and X-22-2475 (produced by Shin-Etsu Silicone Co., Ltd.), Silaplane FM-0711, FM-0721, FM-0725, TM-0701, and TM-0701T (produced by Chisso Corporation), and AK-5 and AK-30 (produced by Toagosei Co., Ltd.), can be used as they are.

The polyfluoroalkyl alcohol(meth)acrylic acid derivative [I] and the polysiloxane containing a terminal (meth)acryloyloxy group [II] can be copolymerized in any ratio. More specifically, the weight ratio of [I] to [II] is 1 to 99:99 to 1, preferably 30 to 95:70 to 5, more preferably 70 to 90:30 to 10, proviso that the total of [I] and [II] is 100. The copolymerization ratio thereof is determined by the relationship between the water- and oil-repellent performance and the affinity for powder of the fluorine-containing copolymer. When the copolymerization ratio of the silicone monomer [II] is less than this range, affinity shown by smoothness and adhesion is insufficient when the fluorine-containing copolymer is used as a surface-treatment agent for powder.

The copolymer can be further copolymerized with a fluorine atom-free polymerizable monomer and/or another fluorine-containing polymerizable monomer. When another fluorine-containing polymerizable monomer is used, the number of carbon atoms of the polyfluoroalkyl group, preferably perfluoroalkyl group, of the monomer must be 1 to 6, preferably 2 to 4.

As the fluorine atom-free polymerizable monomer to be copolymerized with the polyfluoroalkyl alcohol(meth)acrylic acid derivative [I] and the polysiloxane containing a terminal (meth)acryloyloxy group [II], at least one of (meth)acrylic acid esters represented by the following general formulae [III], [IV], and [V] is preferably used.

  [III]

  [IV]

  [V]

$R^1$: H or a methyl group
$R^3$: a $C_1$-$C_{30}$ linear, branched, or alicyclic alkyl group or an aralkyl group
$R^6$: a $C_1$-$C_{30}$ linear or branched alkylene group
$R^7$: a $C_1$-$C_6$ linear or branched alkylene group
$R^8$: a $C_1$-$C_{30}$ linear or branched alkyl group or an aromatic group
Y: a crosslinkable functional group
l: an integer of 1 to 50

Moreover, examples of the fluorine atom-free polymerizable monomer, including the above compounds [III], [IV], and [V], are acrylic acid esters or methacrylic acid esters etherified with alkyl groups, such as methyl, ethyl, propyl, isopropyl, n-butyl, n-hexyl, 2-ethylhexyl, n-octyl, lauryl, and stearyl; cycloalkyl groups, such as cyclohexyl; aralkyl groups, such as benzyl; alkoxyalkyl groups, such as methoxymethyl, 2-methoxyethyl, 2-ethoxyethyl, 2-butoxyethyl, and 3-ethoxypropyl; fumaric acid or maleic acid ester esterified with monoalkyl esters or dialkyl esters, such as monomethyl, dimethyl, monoethyl, diethyl, monopropyl, dipropyl, monobutyl, dibutyl, mono-2-ethylhexyl, di-2-ethylhexyl, monooctyl, and dioctyl; and vinyl esters, such as vinyl acetate and vinyl caprylate. Preferably, alkyl(meth)acrylate containing a long chain alkyl group having 8 or more carbon atoms are used. Specific examples thereof include acrylic acid esters etherified with alkyl groups, such as 2-ethylhexyl, n-octyl, lauryl, and stearyl; cycloalkyl groups, such as cyclohexyl; and aralkyl groups, such as benzyl. More preferably, a combination of an acrylic acid ester etherified with an alkyl group, such as 2-ethylhexyl or stearyl, and a (meth)acrylic acid ester etherified with an aralkyl group, such as benzyl, is used in terms of the balance between water-repellency and oil-repellency.

Usable fluorine-containing polymerizable monomers are represented by the general formula:

$$CH_2=CRCOOR^9(NR^{10}SO_2)_mRf \quad [VI]$$

R: a hydrogen atom or a methyl group
$R^9$: a linear or branched alkylene group having 1 to 6 carbon atoms
$R^{10}$ a lower alkyl group having 1 to 4 carbon atoms
Rf: a polyfluoroalkyl group, preferably a perfluoroalkyl group, having 1 to 6 carbon atoms, preferably 2 to 4 carbon atoms
m: 0 or 1.

For example, polyfluoroalkyl group-containing (meth)acrylate monomers shown in paragraph [0018] of Patent Document 1 can be used. However, the number of carbon atoms n of the terminal polyfluoroalkyl group must be 1 to 6. When $R^9$ is a polyfluoroalkylene group, the total number of carbon atoms of the polyfluoroalkylene group and the terminal polyfluoroalkyl group must be 2 to 6.

Further, if necessary, a polyfunctional monomer or oligomer can be copolymerized in a ratio of 10 wt. % or less in the copolymer. Examples of the polyfunctional monomer or oligomer include ethyleneglycol di(meth)acrylate, propyleneglycol di(meth)acrylate, 1,4-butanediol di(meth)acrylate, 1,6-hexanediol di(meth)acrylate, 1,9-nonanediol di(meth)acrylate, neopentylglycol di(meth)acrylate, tetraethyleneglycol di(meth)acrylate, tripropyleneglycol di(meth)acrylate, polypropyleneglycol di(meth)acrylate, Bisphenol A.ethylene oxide adduct diacrylate, dimethylol tricyclodecane diacrylate, glycerin methacrylate acrylate, 3-acryloyloxyglycerin monomethacrylate, and the like.

In terms of cost, a copolymer with a fluorine atom-free polymerizable comonomer is advantageous. It is preferable, in terms of both water- and oil-repellency and cost, to copolymerize a fluorine atom-free polymerizable monomer in about 30 wt. % or less, preferably about 10 to 30 wt. %, in the copolymer.

Furthermore, a crosslinkable group-containing monomer, such as (meth)acrylamide, N-methylol(meth)acrylamide, N-methoxymethyl acrylamide, N-butoxymethyl acrylamide, or glycidyl(meth)acrylate, can be added and copolymerized in a ratio of about 10 wt. % or less, preferably about 0.5 to 7 wt. %, in the copolymer. When such a crosslinkable group-containing monomer is further copolymerized, crosslinking with the hydroxyl group on the fiber surface or self-crosslinking occurs to thereby enhance the durability of the water- and oil-repellent.

Although the copolymerization reaction may be performed by emulsion polymerization or suspension polymerization, the reaction is preferably performed by solution polymerization. Usable reaction solvents for solution polymerization are hydrocarbon-based solvents, alcohol-based solvents, ester-based solvents, ketone-based solvents, hydrofluorocarbon-based solvents, hydrofluoroether-based solvents, etc. These solvents can be used singly or in combination of two or more.

Examples of hydrocarbon-based solvents include linear or branched aliphatic hydrocarbons having 5 to 16 carbon atoms; alicyclic hydrocarbons, such as cyclopentane, cyclohexane, and methyl or ethyl derivatives thereof; aromatic hydrocarbons, such as benzene, toluene, and xylene; trifluoromethyl group-substituted aromatic hydrocarbons, such as 1,4-bis(trifluoromethyl)benzene and 1,3-bis(trifluoromethyl)benzene; and the like.

Examples of alcohol-based solvents include linear or branched alkanols having 1 to 8 carbon atoms. Alkanols may be 1-alkanol, 2-alkanol, and the like.

Examples of ester-based solvents include methyl, ethyl, propyl, and butyl esters of acetic acid; methyl propionate; methyl, ethyl, and pentyl esters of lactic acid; and the like.

Examples of ketone-based solvents include acetone, methyl ethyl ketone, methyl isobutyl ketone, 2-pentanone, 3-pentanone, 2-hexanone, and the like.

Examples of hydrofluorocarbon-based solvents are as follows.

| | | |
|---|---|---|
| $CF_3CF_2CF_2CHF_2$ | $CF_3CF_2CF_2CH_2F$ | $CF_3CF_2CH_2CF_3$ |
| $CHF_2CF_2CF_2CHF_2$ | $CHF_2CH_2CF_2CF_3$ | $CF_3CHFCH_2CF_3$ |
| $CF_3CH_2CF_2CHF_2$ | $CHF_2CHFCF_2CHF_3$ | $CF_3CHFCF_2CH_3$ |
| $CHF_2CHFCHFCHF_2$ | $CF_3CH_2CF_2CH_3$ | $CF_3CF_2CH_2CH_3$ |
| $CHF_2CH_2CF_2CH_3$ | $CHF_2CF_2CF_2CF_3$ | $CF_3CF_2CF_2CHFCF_3$ |
| $CHF_2CF_2CF_2CF_2CHF_2$ | $CF_3CHFCHFCF_2CF_3$ | $CF_3CHFCF_2CH_2CF_3$ |
| $CF_3CF(CF_3)CH_2CHF_2$ | $CF_3CF(CF_3)CH_2CF_3$ | $CF_3CH_2CF_2CH_2CF_3$ |
| $CHF_2CHFCF_2CHFCHF_2$ | $CHF_2CF_2CF_2CHFCH_3$ | |
| $CF_3CH_2CH_2CH_2CF_3$ | $CHF_2CH_2CF_2CH_2CHF_2$ | |
| $CF_3(CF_2)_4CHF_2$ | $CF_3(CF_2)_4CH_2F$ | |
| $CHF_2(CF_2)_4CHF_2$ | $CF_3CF_2CF_2CF_2CH_2CF_3$ | |
| $CF_3CH(CF_3)CHFCF_2CF_3$ | | |
| $CF_3CF_2CH_2CH(CF_3)CF_3$ | $CF_3CH_2CF_2CF_2CH_2CF_3$ | |
| $CF_3CF_2CH_2CH_2CF_2CF_3$ | $CF_3CF_2CF_2CF_2CH_2CH_3$ | |
| $CF_3CH(CF_3)CH_2CH_2CF_3$ | $CHF_2CF_2CH_2CH_2CF_2CHF_2$ | |
| $CF_3CF_2CF_2CH_2CH_2CH_3$ | | |

Moreover, examples of hydrofluoroethers-based solvent are as follows:

| | | |
|---|---|---|
| $CF_3CF_2CF_2OCH_3$ | $(CF_3)_2CFOCH_3$ | $CF_3CF_2CF_2OCH_2CH_3$ |
| $CF_3CF_2CF_2CF_2OCH_3$ | $(CF_3)_2CFCF_2OCH_3$ | $(CF_3)_3COCH_3$ |

-continued
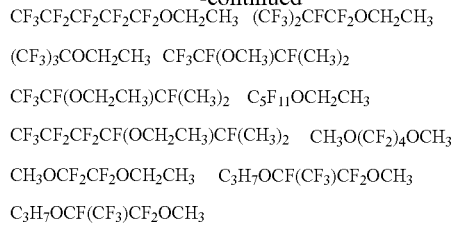

CF₃CF₂CF₂CF₂CF₂OCH₂CH₃  (CF₃)₂CFCF₂OCH₂CH₃

(CF₃)₃COCH₂CH₃  CF₃CF(OCH₃)CF(CH₃)₂

CF₃CF(OCH₂CH₃)CF(CH₃)₂  C₅F₁₁OCH₂CH₃

CF₃CF₂CF₂CF(OCH₂CH₃)CF(CH₃)₂  CH₃O(CF₂)₄OCH₃

CH₃OCF₂CF₂OCH₂CH₃  C₃H₇OCF(CF₃)CF₂OCH₃

C₃H₇OCF(CF₃)CF₂OCH₃

As an initiator used in an amount of about 0.1 to 4 wt. %, preferably about 1 to 2 wt. %, based on the total amount of the comonomers, diacyl peroxide, peroxy carbonate, peroxy ester, or the like is used. Specific examples thereof include organic peroxides, such as isobutyryl peroxide, lauroyl peroxide, stearoyl peroxide, succinic acid peroxide, bis(heptafluorobutyryl)peroxide, pentafluorobutyroyl peroxide, bis(4-tert-butylcyclohexyl)peroxydicarbonate, di-n-propyl peroxydicarbonate, and diisopropyl peroxydicarbonate. Depending on the polymerization method, an azo compound, inorganic peroxide, or a redox system thereof can also be used. The polymerization reaction may be less likely to progress depending on the reaction conditions and composition ratio; however, in that case, a polymerization initiator can be added again in the middle of the polymerization reaction.

Moreover, in order to adjust the molecular weight, a chain transfer agent can be used, if necessary. Examples of the chain transfer agent include dimethyl ether, methyl tert-butyl ether, $C_1$-$C_6$ alkanes, methanol, ethanol, 2-propanol, cyclohexane, carbon tetrachloride, chloroform, dichloromethane, methane, ethyl acetate, ethyl malonate, acetone, and the like.

The copolymerization reaction is carried out using these reaction solvents, reaction initiators, etc., at a reaction temperature of about 0 to 100° C., preferably about 5 to 60° C., particularly preferably about 40 to 50° C. After completion of the reaction, a copolymer solution having a solid matters content of about 5 to 30 wt. % is obtained, and the solvent is removed from the reaction mixture, thereby obtaining a fluorine-containing copolymer.

As a result of analysis of the remaining unreacted comonomer by gas chromatography, it was confirmed that the polyfluoroalkyl alcohol (meth)acrylic acid derivative [I] used in the copolymerization reaction was almost completely copolymerized.

The thus-obtained fluorine-containing copolymer is separated by evaporation to dryness, and purified by washing with a solvent or the like. The weight-average molecular weight (Mw; polystyrene conversion) of the obtained fluorine-containing copolymer, which is shown by high-performance liquid chromatography, is about 10,000 to 1,000,000.

Since the fluorine-containing copolymer is preferably obtained as a polymer solution by solution polymerization, or the like, the polymer solution is diluted with a fluorine-containing organic solvent, such as 1,4-bis(trifluoromethyl)benzene or 1,3-bis(trifluoromethyl)benzene, so that the solid matters content is about 0.01 to 30 wt. %, preferably about 0.05 to 5 wt. %, for use as a water- and oil-repellent. A polymerization product obtained by water-based emulsion polymerization, suspension polymerization, or other methods, other than solution polymerization, can also be used. In this case, a flocculant is added to a polymerization reaction solution to coagulate a polymerization product, and the polymerization product is washed with water or an organic solvent to separate a fluorine-containing copolymer. The separated fluorine-containing copolymer is dissolved in a fluorine-containing organic solvent. Thus, a water- and oil-repellent comprising the organic solvent solution can be prepared.

The water- and oil-repellent comprising the fluorine-containing copolymer as an active ingredient and composed of a fluorine-containing organic solvent solution of the copolymer can further contain other additives that are necessary for use as water- and oil-repellents. Examples of such additives include crosslinking agents, such as melamine resin, urea resin, and blocked isocyanate; polymer extenders; silicone resin or other water-repellents, such as oil and wax; insecticides, antistatic agents, dye stabilizers, crease-preventing agents, stain blockers, and the like.

The thus-obtained water- and oil-repellent can be effectively applied to, for example, paper, films, fiber, fabric, woven fabric, carpet, and textile products made of filament, fiber, or yarn. As the application method, coating, immersion, spraying, padding, roll coating, or a combination thereof is generally used. For example, the water- and oil-repellent is used as a pad bath by preparing a bath having a solid matters content of about 0.1 to 10 wt. %. A material to be treated is padded in the pad bath, and then the excess solution is removed by squeeze rolls, followed by drying, so that the amount of the polymer attached to the material to be treated is about 0.01 to 10 wt. %. Subsequently, drying of the material is generally carried out at a temperature of about 100 to 200° C. for about 1 minute to 2 hours, although the drying conditions vary depending on the type of material to be treated. Then, the water- and oil-repellent treatment is completed.

The fluorine-containing copolymer of the present invention can be further used as a surface-treatment agent for various inorganic pigment-containing powders, such as talc, kaolin, mica, titanium mica, titanium oxide, iron oxide, and zinc oxide, used in foundations and other cosmetics, so as to improve their water resistance and oil repellency.

In this case, the fluorine-containing copolymer can be used in combination with Vaseline, lanolin, ceresin, and other higher fatty acids or salts thereof; liquid oils, such as squalane, liquid paraffin, ester oil, diglyceride, triglyceride, and silicone oil; fluorine-based oilnesses, such as perfluoropolyether oils; as well as surfactants, organic dyes or pigments, ethanol, preservatives, antioxidants, thickeners, pH adjustors, flavoring agents, ultraviolet absorbers, moisturizers, blood-circulation promoters, cold sensation-imparting agents, antiperspirants, disinfectants, skin activators, and the like.

EXAMPLES

The present invention will be described with reference to examples below.

Synthesis Example 1

(1) In a 1200-mL autoclave equipped with a stirrer and a thermometer, 603 g (1.17 mol) of

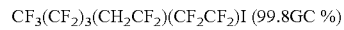

CF₃(CF₂)₃(CH₂CF₂)(CF₂CF₂)I (99.8GC %)

and 7 g of di-tertiary butyl peroxide were charged, and the autoclave was deaerated with a vacuum pump. When the inner temperature was increased to 80° C., ethylene was sequentially introduced into the autoclave to adjust the inner pressure to 0.5 MPa. When the inner pressure was decreased to 0.2 MPa, ethylene was introduced again to increase the inner pressure to 0.5 MPa. This process was repeated to introduce 49 g (1.7 mol) of ethylene over about 3 hours, while maintaining the inner temperature at 80 to 115° C. The content was collected at an inner temperature of 50° C. or lower to obtain 635 g (yield: 98.8%) of $CF_3(CF_2)_3(CH_2CF_2)(CF_2CF_2)(CH_2CH_2)I$ (98.3GC %).

(2) In a 200-mL three-neck flask equipped with a condenser and a thermometer, 100 g (0.18 mol) of $CF_3(CF_2)_3(CH_2CF_2)(CF_2CF_2)(CH_2CH_2)I$ (98.3GC %)

prepared in the above (1) and 100 g (1.68 mol) of N-methyl formamide were charged, followed by stirring at 150° C. for 4 hours. After the completion of the reaction, the reaction mixture was washed with 30 mL of water. The lower layer (82.8 g) was mixed with 83 g of a 15 wt % p-toluenesulfonic acid aqueous solution, followed by stirring at 80° C. for 8 hours. The reaction mixture was left at rest, and then 60 g of a reaction product (78.4GC %), being a transparent, colorless liquid at room temperature, was obtained as the lower layer (yield: 62.6%).

The reaction product was subjected to reduced pressure distillation under conditions of an inner pressure of 0.2 kPa, an inner temperature of 100 to 144° C., and a column top temperature of 58 to 59° C. to obtain 43.7 g (distillation yield: 88.2%) of a purified reaction product (95.4GC %).

The resulting purified reaction product was confirmed by the results of $^1$H-NMR and $^{19}$F-NMR to be the compound represented by the following formula:

$CF_3(CF_2)_3(CH_2CF_2)(CF_2CF_2)(CH_2CH_2)OH$ (3) 40.0 g (0.09 mol) of the reaction product (95.4GC %) prepared in the above (2), 21 g of toluene, 1.7 g of p-toluenesulfonic acid, and 0.05 g of hydroquinone were charged in a 100-mL three-neck flask equipped with a condenser and a thermometer. After the inner temperature was increased to 100° C., 10.2 g (0.14 mol) of acrylic acid was added in the flask, followed by stirring at an inner temperature of 115° C. for 2 hours. After the completion of the reaction, 72 g of the reaction solution was collected after cooling. Toluene was removed with an evaporator, and 44.5 g of the residue was washed with tap water to obtain 40.9 g (yield: 82.6%) of a reaction product (86.3GC %), being a transparent, colorless liquid at room temperature, was obtained as the lower layer.

The reaction product was subjected to reduced pressure distillation under conditions of an inner pressure of 0.2 kPa, an inner temperature of 103 to 143° C., and a column top temperature of 60 to 61° C. to obtain 15.7 g (distillation yield: 44.1%) of a purified reaction product (99.2GC %).

The resulting purified reaction product was confirmed by the results of $^1$H-NMR and $^{19}$F-NMR to be the compound represented by the following formula:

$CF_3(CF_2)_3(CH_2CF_2)(CF_2CF_2)(CH_2CH_2)OCOCH=CH_2$

[Fluorine-Containing Monomer A]

Synthesis Example 2

(1) A reaction for introducing 34 g (1.2 mol) of ethylene was performed, as in Synthesis Example 1 (1), using 529 g (0.86 mol) of $CF_3(CF_2)_3(CH_2CF_2)(CF_2CF_2)_2I$ (99.9GC %)

and 5 g of the di-tertiary butyl peroxide to obtain 550 g (yield: 99.4%) of $CF_3(CF_2)_3(CH_2CF_2)(CF_2CF_2)_2(CH_2CH_2)I$ (99.1GC %).

(2) In a 200-mL three-neck flask equipped with a condenser and a thermometer, 150 g (0.24 mol) of $CF_3(CF_2)_3(CH_2CF_2)(CF_2CF_2)_2(CH_2CH_2)I$ (99.1 GC%)

prepared in the above (1) and 105 g (1.78 mol) of N-methyl formamide were charged, followed by stirring at 150° C. for 5 hours. After the completion of the reaction, the reaction mixture was washed with 40 mL of water. The lower layer (132.3 g) was mixed with 135 g of a 15 wt % p-toluenesulfonic acid aqueous solution, followed by stirring at 80° C. for 7 hours. The reaction mixture was left at rest, and then 103 g (yield: 53.5%) of a reaction product (65.5GC %), being a white solid, was obtained as the lower layer.

The reaction product was subjected to reduced pressure distillation under conditions of an inner pressure of 0.2 kPa, an inner temperature of 121 to 163° C., and a column top temperature of 76 to 77° C. to obtain 66.9 g (distillation yield: 94.2%) of a purified reaction product (95.3GC %).

The resulting purified reaction product was confirmed by the results of $^1$H-NMR and $^{19}$F-NMR to be the compound represented by the following formula:

$CF_3(CF_2)_3(CH_2CF_2)(CF_2CF_2)_2(CH_2CH_2)OH$ (3) 60.0 g (0.11 mol) of the reaction product (95.4GC %) prepared in the above (2), 29 g of toluene, 1.6 g of p-toluenesulfonic acid, and 0.07 g of hydroquinone were charged in a 100-mL three-neck flask equipped with a condenser and a thermometer. After the inner temperature was increased to 100° C., 10 g (0.14 mol) of acrylic acid was added in the flask, followed by stirring at an inner temperature of 118° C. for 3 hours. After the completion of the reaction, 82 g of the reaction solution was collected after cooling. Toluene was removed with an evaporator, and 63.9 g of the residue was washed with tap water to obtain 60.8 g (yield: 86.4%) of a reaction product (89.3GC %), being a transparent, colorless liquid at room temperature, was obtained as the lower layer.

The reaction product was subjected to reduced pressure distillation under conditions of an inner pressure of 0.2 kPa, an inner temperature of 125 to 155° C., and a column top temperature of 84 to 86° C. to obtain 42.2 g (distillation yield: 77.2%) of a purified reaction product (99.4GC %).

The resulting purified reaction product was confirmed by the results of $^1$H-NMR and $^{19}$F-NMR to be the compound represented by the following formula:

$CF_3(CF_2)_3(CH_2CF_2)(CF_2CF_2)_2(CH_2CH_2)OCOCH=CH_2$

[Fluorine-Containing Monomer B]

Synthesis Example 3

60.0g (0.11 mol) of the reaction product (95.4GC %) prepared in Synthesis Example 2 (2), 29 g of toluene, 1.6 g of p-toluenesulfonic acid, and 0.07 g of hydroquinone were charged in a 100-mL three-neck flask equipped with a condenser and a thermometer. After the inner temperature was increased to 100° C., 12 g (0.14 mol) of methacrylic acid was added in the flask, followed by stirring at an inner temperature of 118° C. for 3 hours. After the completion of the reaction, 82 g of the reaction solution was collected after cooling. Toluene was removed with an evaporator, and 64 g of the residue was washed with tap water to obtain 60.8 g (yield: 86%) of a reaction product (89GC %), being a transparent, colorless liquid at room temperature, was obtained as the lower layer.

The reaction product was subjected to reduced pressure distillation under conditions of an inner pressure of 0.2 kPa, an inner temperature of 125 to 155° C., and a column top temperature of 84 to 86° C. to obtain 42.2 g (distillation yield: 77.2%) of a purified reaction product (99.4GC %).

The resulting purified reaction product was confirmed by the results of $^1$H-NMR and $^{19}$F-NMR to be the compound represented by the following formula:

CF$_3$(CF$_2$)$_3$(CH$_2$CF$_2$)(CF$_2$CF$_2$)(CH$_2$CH$_2$)OCOCH=CH$_2$

[Fluorine-Containing Monomer C]

Synthesis Example 4

(1) In a 1200-mL autoclave equipped with a stirrer and a thermometer, 603 g (1.17 mol) of

CF$_3$(CF$_2$)(CH$_2$CF$_2$)(CF$_2$CF$_2$)$_2$I (97GC %)

and 7 g of di-tertiary butyl peroxide were charged, and the autoclave was deaerated with a vacuum pump. When the inner temperature was increased to 80° C., ethylene was sequentially introduced into the autoclave to adjust the inner pressure to 0.5 MPa. When the inner pressure was decreased to 0.2 MPa, ethylene was introduced again to increase the inner pressure to 0.5 MPa. This process was repeated to introduce 49 g (1.7 mol) of ethylene over about 3 hours, while maintaining the inner temperature at 80 to 115° C. The content was collected at an inner temperature of 50° C. or lower to obtain 630 g (yield: 98.8%) of

CF$_3$(CF$_2$)(CH$_2$CF$_2$)(CF$_2$CF$_2$)$_2$(CH$_2$CH$_2$)I (98GC %).

(2) In a 200-mL three-neck flask equipped with a condenser and a thermometer, 100 g (0.18 mol) of

CF$_3$(CF$_2$)(CH$_2$CF$_2$)(CF$_2$CF$_2$)$_2$(CH$_2$CH$_2$)I (98GC %)

prepared in the above (1) and 100 g (1.68 mol) of N-methyl formamide were charged, followed by stirring at 150° C. for 4 hours. After the completion of the reaction, the reaction mixture was washed with 30 mL of water. The lower layer (82.8 g) was mixed with 83 g of a 15 wt % p-toluenesulfonic acid aqueous solution, followed by stirring at 80° C. for 8 hours. The reaction mixture was left at rest, and then 60 g (yield: 62%) of a reaction product (78GC %), being a transparent, colorless liquid at room temperature, was obtained as the lower layer.

The reaction product was subjected to reduced pressure distillation under conditions of an inner pressure of 0.2 kPa, an inner temperature of 100 to 144° C., and a column top temperature of 58 to 59° C. to obtain 43 g (distillation yield: 88%) of a purified reaction product (95GC %).

The resulting purified reaction product was confirmed by the results of $^1$H-NMR and $^{19}$F-NMR to be the compound represented by the following formula:

CF$_3$(CF$_2$)(CH$_2$CF$_2$)(CF$_2$CF$_2$)$_2$(CH$_2$CH$_2$)OH (3) 40.0g (0.09 mol) of the reaction product (95GC %) prepared in the above (2), 21 g of toluene, 1.7 g of p-toluenesulfonic acid, and 0.05 g of hydroquinone were charged in a 100-mL three-neck flask equipped with a condenser and a thermometer. After the inner temperature was increased to 100° C., 10.2 g (0.14 mol) of acrylic acid was added in the flask, followed by stirring at an inner temperature of 115° C. for 2 hours. After the completion of the reaction, 72 g of the reaction solution was collected after cooling. Toluene was removed with an evaporator, and 44.5 g of the residue was washed with tap water to obtain 41 g (yield: 82%) of a reaction product (86GC %), being a transparent, colorless liquid at room temperature, was obtained as the lower layer.

The reaction product was subjected to reduced pressure distillation under conditions of an inner pressure of 0.2 kPa, an inner temperature of 103 to 143° C., and a column top temperature of 60 to 61° C. to obtain 16 g (distillation yield: 44%) of a purified reaction product (99GC %).

The resulting purified reaction product was confirmed by the results of $^1$H-NMR and $^{19}$F-NMR to be the compound represented by the following formula:

CF$_3$(CF$_2$)$_3$(CH$_2$CF$_2$)(CF$_2$CF$_2$)(CH$_2$CH$_2$)OCOCH=CH$_2$

[Fluorine-Containing Monomer D]

Example 1

| | |
|---|---|
| Fluorine-containing monomer A obtained in Synthesis Example 1 | 50 g |
| Methacrylic acid terminal-dimethylpolysiloxane-type silicone monomer (X-22-174DX, produced by Shin-Etsu Chemical Co., Ltd.; viscosity (25° C.): 60 mm$^2$/sec, specific gravity (25° C.): 0.97, refractive index (25° C.): 1.407, functional group equivalent weight: 4,600 g/mol) | 50 g |
| 1,4-bis(trifluoromethyl)benzene | 350 g |

The above components were charged in a 500-ml reactor equipped with a condenser, and the reactor was purged with nitrogen gas for 30 minutes. Further,

| | |
|---|---|
| bis(4-tert-butylcyclohexyl)peroxydicarbonate | 1.0 g | was added to the reactor (total: 451.0 g), and the temperature in the reactor was gradually raised to 50° C. A polymerization reaction was carried out at this temperature for 16 hours while stirring.

After completion of the reaction, the reactor was cooled, thereby obtaining a polymer solution having a solid matters content of 21.6 wt. %. As a result of analyzing the remaining unreacted comonomer by gas chromatography, it was confirmed that 99% of the fluorine-containing monomer A used in the copolymerization reaction was copolymerized.

The obtained copolymer solution was placed in a 120° C. oven, and the solvent was removed to isolate a fluorine-containing monomer A/silicone monomer copolymer, which had a weight-average molecular weight (Mw) of 91,000. Here, Mw was measured by a GPC measuring method using Shodex GPC KD 806M +KD-802 +KD-G at a temperature of 40° C. with an eluate of a 10 mM tetrahydrofuran solution at an elution rate of 1 ml/min. The detector used was a differential refractometer, and the analysis was performed by Lab-chart 180 (polystyrene conversion) produced by SIC.

To the copolymer solution, 1,4-bis(trifluoromethyl)benzene was added so that the solid matters content was diluted to 2 wt. %. The resulting diluted solution (1 ml) was applied to a stainless steel plate (2×5 cm) and dried at 120° C. for 30 minutes, thereby preparing a test piece.

The prepared test piece was subjected to a measurement of the static contact angle (by a sessile-drop method), which was an indicator of water- and oil-repellent performance, for water and tetradecane, and a four-step evaluation was carried out according to the following criteria:

| Evaluation | Water (water-repellency) | Tetradecane (oil-repellency) |
|---|---|---|
| ☺ | 110-130° | 70° or more |
| ○ | 90-109° | 60-69° |
| Δ | 70-89° | 50-59° |
| X | 69° or less | 49° or less |

In addition, the copolymer solution was cast on a PET film and dried at 120° C. for 2 hours, thereby obtaining a copolymer film. In order to evaluate the water resistance, the film was immersed in water for 10 minutes and allowed to stand for one day. Thereafter, the contact angle was measured, and the rate of change in the contact angle before and after immersion in water was evaluated as follows: less than 3%: ⊚; 3% to less than 5%: ○; 5% to less than 10%: Δ; and 10% or more: ×.

Example 2

A copolymerization reaction was carried out as in Example 1 except that 70 g of the fluorine-containing monomer B obtained in Synthesis Example 2 was used in place of the fluorine-containing monomer A, and the amount of silicone monomer was changed to 30 g.

Example 3

A copolymerization reaction was carried out as in Example 1 except that 30 g of the fluorine-containing monomer C obtained in Synthesis Example 3 was used in place of the fluorine-containing monomer A, and the amount of silicone monomer was changed to 70 g.

Example 4

A copolymerization reaction was carried out as in Example 1 except that 90 g of the fluorine-containing monomer D obtained in Synthesis Example 4 was used in place of the fluorine-containing monomer A, and the amount of silicone monomer was changed to 10 g.

Example 5

A copolymerization reaction was carried out as in Example 1 except that 70 g of the fluorine-containing monomer B was used in place of the fluorine-containing monomer A, the amount of silicone monomer was changed to 20 g, and 10 g of stearyl methacrylate [StMA] was further used.

Example 6

A copolymerization reaction was carried out as in Example 1 except that 80 g of the fluorine-containing monomer C was used in place of the fluorine-containing monomer A, the amount of silicone monomer was changed to 10 g, and 10 g of benzyl methacrylate [BzMA] was further used.

Example 7

A copolymerization reaction was carried out as in Example 1 except that 50 g of the fluorine-containing monomer D was used in place of the fluorine-containing monomer A, the amount of silicone monomer was changed to 30 g, and 20 g of 2-ethylhexyl methacrylate [EHMA] was further used.

Example 8

A copolymerization reaction was carried out as in Example 1 except that the amount of fluorine-containing monomer A was changed to 70 g, the amount of silicone monomer was changed to 10 g, respectively, and 10 g of benzyl methacrylate [BzMA], 5 g of 2-hydroxyethyl acrylate [2HEA], and 5 g of polyethyleneglycol (n=4) monomethacrylate [PE-200] were further used.

Reference Example 1

A copolymerization reaction was carried out as in Example 1 except that 70 g of 2-(n-perfluorooctyl)ethyl acrylate [FAAC-8] was used in place of the fluorine-containing monomer A, and the amount of silicone monomer was changed to 30 g.

Reference Example 2

A copolymerization reaction was carried out as in Example 1 except that 70 g of 2-(n-perfluorohexyl)ethyl methacrylate [FAMAC-6] was used in place of the fluorine-containing monomer A, and the amount of silicone monomer was changed to 30 g.

Reference Example 3

A copolymerization reaction was carried out as in Example 1 except that 70 g of FAAC-8 was used in place of the fluorine-containing monomer A, and 30 g of StMA was used in place of the silicone monomer.

Reference Example 4

A copolymerization reaction was carried out as in Example 1 except that the amount of fluorine-containing monomer A was changed to 70 g, and 30 g of StMA was used in place of the silicone monomer.

Table 1 below shows the measurement and evaluation results of the static contact angle (water- and oil-repellent performance) and water resistance obtained in the above Examples and Reference Examples, as well as the composition of the monomers used in the copolymerization reaction (unit: g).

TABLE 1

| | Ex. | | | | | | | | Ref. Ex. | | | |
|---|---|---|---|---|---|---|---|---|---|---|---|---|
| | 1 | 2 | 3 | 4 | 5 | 6 | 7 | 8 | 1 | 2 | 3 | 4 |
| [Copolymerization monomer] | | | | | | | | | | | | |
| Fluorine-containing monomer A | 50 | — | — | — | — | — | — | 70 | — | — | — | 70 |
| Fluorine-containing monomer B | — | 70 | — | — | 70 | — | — | — | — | — | — | — |
| Fluorine-containing monomer C | — | — | 30 | — | — | 80 | — | — | — | — | — | — |
| Fluorine-containing monomer D | — | — | — | 90 | — | — | 50 | — | — | — | — | — |
| FAAC-8 | — | — | — | — | — | — | — | — | 70 | — | 70 | — |
| FAMAC-6 | — | — | — | — | — | — | — | — | — | 70 | — | — |
| Silicone monomer | 50 | 30 | 70 | 10 | 20 | 10 | 30 | 10 | 30 | 30 | — | — |
| StMA | — | — | — | — | 10 | — | — | — | — | — | 30 | 30 |
| BzMA | — | — | — | — | — | 10 | — | 10 | — | — | — | — |
| EHMA | — | — | — | — | — | — | 20 | — | — | — | — | — |
| 2HEA | — | — | — | — | — | — | — | 5 | — | — | — | — |
| PE-200 | — | — | — | — | — | — | — | 5 | — | — | — | — |
| [Water- and oil-repellent performance] | | | | | | | | | | | | |
| Water-repellency | ⊚ | ⊚ | ⊚ | ⊚ | ⊚ | ⊚ | ⊚ | ⊚ | ⊚ | ○ | ⊚ | ⊚ |
| Oil-repellency | ○ | ⊚ | ○ | ⊚ | ⊚ | ⊚ | ○ | ⊚ | ⊚ | Δ | ⊚ | ⊚ |
| Water resistance | ⊚ | ⊚ | ⊚ | ⊚ | ⊚ | ⊚ | ○ | ○ | ⊚ | ○ | ⊚ | ⊚ |

The above results demonstrate that Examples 3 and 6, which used the fluorine-containing monomer C containing a terminal methacrylate group, showed superior water-repellency, oil-repellency, and water resistance to those of Reference Example 2, which used a 2-(n-perfluorohexyl)ethyl methacrylate copolymer.

Examples 9 to 11 and Comparative Examples 1 to 4

(1) Two parts by weight of the copolymer obtained in each of the Examples and Reference Examples or dimethylpolysiloxane (KF-96A, produced by Shin-Etsu Chemical Co., Ltd.; 6 mm²/s), 48 parts by weight of mica, and 50 parts by weight of isopropanol were placed in a mixer, and the isopropanol was distilled off under reduced pressure while heating to 80° C. Thus, powders A to G were obtained.

TABLE 2

| Powder | Polymer component |
|---|---|
| A | Copolymer obtained in Example 2 |
| B | Copolymer obtained in Example 5 |
| C | Copolymer obtained in Example 8 |
| D | Copolymer obtained in Reference Example 1 |
| E | Copolymer obtained in Reference Example 3 |
| F | Copolymer obtained in Reference Example 4 |
| G | Dimethylpolysiloxane |

(2) To 50 parts by weight of each of the above-obtained powders, the following components were added (total: 100 parts by weight).

| | |
|---|---|
| Titanium oxide | 16 parts by weight |
| Vaseline | 3 parts by weight |
| Talc | 10 parts by weight |
| Iron oxide | 10 parts by weight |
| Dimethylpolysiloxane | 6 parts by weight |
| Liquid paraffin | 5 parts by weight |

Each of the components was mixed with a mixer so that the mixture was homogeneous, and then press-molded in a mold, thereby obtaining a foundation powder product.

The thus-obtained powder products were subjected to measurement and evaluation of water-repellency and oil-repellency in the same manner as described above, and the smoothness of powder and adhesion were evaluated.

Smoothness and adhesion: Five professional panelists evaluated the texture of the powders (e.g., smoothness of powder and adhesion to the skin) on a five-point scale (5: very good, 4: good, 3: average, 2: bad, 1: very bad), and the average marks were evaluated as follows:

| Evaluation | Average |
|---|---|
| ◎ | 4.5-5.0 |
| ○ | 3.5-less than 4.5 |
| Δ | 2.5-less than 3.5 |
| X | 1.5-less than 2.5 |
| XX | Less than 1.5 |

(3) Table 3 below shows the measurement and evaluation results and the type of powder used.

TABLE 3

| | Ex. 9 | Ex. 10 | Ex. 11 | Comp. Ex. 1 | Comp. Ex. 2 | Comp. Ex. 3 | Comp. Ex. 4 |
|---|---|---|---|---|---|---|---|
| [Powder] | | | | | | | |
| Type | A | B | C | D | E | F | G |
| [Measurement and evaluation] | | | | | | | |
| Water-repellency | ◎ | ◎ | ◎ | ◎ | ◎ | ◎ | ○ |
| Oil-repellency | ◎ | ◎ | ○ | ○ | ◎ | ◎ | X |
| Smoothness | ◎ | ◎ | ◎ | Δ | X | X | Δ |
| Adhesion | ◎ | ◎ | ◎ | X | X | X | Δ |

The above results indicate that the powders surface-treated with the fluorine-containing copolymer of the present invention had superior smoothness of powder and adhesion to those of Comparative Example 1, which used the 2-(n-perfluorooctyl)ethyl acrylate copolymer, and Comparative Examples 2 and 3, in which no silicone monomer was copolymerized. Furthermore, as compared with Comparative Example 4, which used dimethylpolysiloxane, the powders surface-treated with the fluorine-containing copolymer of the present invention were superior not only in water-repellency and oil-repellency, but also in smoothness of powder and adhesion.

The invention claimed is:

1. A fluorine-containing copolymer that is a copolymer comprising a polyfluoroalkyl alcohol acrylic or methacrylic acid derivative represented by the general formula:

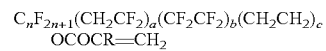

$$C_nF_{2n+1}(CH_2CF_2)_a(CF_2CF_2)_b(CH_2CH_2)_c \\ OCOCR=CH_2 \quad [I]$$

wherein R is a hydrogen atom or a methyl group, n is an integer of 1 to 6, a is an integer of 1 to 4, b is an integer of 1 to 3, and c is an integer of 1 to 3, and a polysiloxane containing a terminal (meth)acryloyloxy group represented by the general formula:

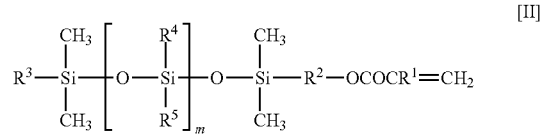

$$R^3-\underset{\underset{CH_3}{|}}{\overset{\overset{CH_3}{|}}{Si}}-\left[O-\underset{\underset{R^5}{|}}{\overset{\overset{R^4}{|}}{Si}}\right]_m-O-\underset{\underset{CH_3}{|}}{\overset{\overset{CH_3}{|}}{Si}}-R^2-OCOCR^1=CH_2 \quad [II]$$

wherein $R^1$ is a hydrogen atom or a methyl group, $R^2$ is a $C_1$-$C_6$ linear or branched divalent alkylene group, $R^3$ is a $C_1$-$C_{30}$ linear or branched alkyl group, $R^4$ and $R^5$ are each a hydrogen atom, a methyl group, or a phenyl group, and m is an integer of 1 to 200.

2. The fluorine-containing copolymer according to claim 1, which has a weight-average molecular weight (Mw) of 10,000 to 1,000,000.

3. The fluorine-containing copolymer according to claim 1, wherein the polyfluoroalkyl alcohol (meth)acrylic acid derivative [I] and the polysiloxane containing a terminal (meth)acryloyloxy group [II] are copolymerized in a weight ratio of 1 to 99:99 to 1.

4. The fluorine-containing copolymer according to claim 1, wherein the polyfluoroalkyl alcohol (meth)acrylic acid derivative [I] and the polysiloxane containing a terminal (meth)acryloyloxy group [II] are copolymerized in a weight ratio of 30 to 95:70 to 5.

5. The fluorine-containing copolymer according to claim 1, which is further copolymerized with at least one monomer of:
an acrylic or methacrylic acid ester [III] represented by the general formula:

$$CH_2=CR^1COOR^3$$

wherein $R^1$ is a hydrogen atom or a methyl group, and $R^3$ is a $C_1$-$C_{30}$ linear, branched, or alicyclic alkyl group or an aralkyl group;
an acrylic or methacrylic acid ester [IV] represented by the general formula:

$$CH_2=CR^1COOR^6Y$$

wherein R1 is a hydrogen atom or a methyl group, $R^6$ is a $C_1$-$C_{30}$ linear or branched alkylene group, and Y is a crosslinkable functional group; and
an acrylic or methacrylic acid ester [V] represented by the general formula:

$$CH_2=CR^1COO(R^7O)_lR^8$$

wherein $R^1$ is a hydrogen atom or a methyl group, $R^7$ is a $C_1$-$C_6$ linear or branched alkylene group, $R^8$ is a hydrogen atom, a $C_1$-$C_{30}$ linear or branched alkyl group, or an aromatic group, and l is an integer of 1 to 50.

6. The fluorine-containing copolymer according to claim 5, wherein at least one of the acrylic acid esters [III], [IV], and [V] is copolymerized in a ratio of 30 wt. % or less in the copolymer.

7. The fluorine-containing copolymer according to claim 6, wherein at least one of the acrylic acid esters [III], [IV], and [V] is copolymerized in a ratio of 10 to 30 wt. % in the copolymer.

8. The fluorine-containing copolymer according to claim 1, which is further copolymerized with a fluorine-containing polymerizable monomer represented by the general formula:

$$CH_2=CRCOOR^9(NR^{10}SO_2)_mRf \qquad [VI]$$

wherein R is a hydrogen atom or a methyl group, $R^9$ is a linear or branched alkylene group having 1 to 6 carbon atoms, $R^{10}$ is a lower alkyl group having 1 to 4 carbon atoms, Rf is a perfluoroalkyl group having 1 to 6 carbon atoms, and m is 0 or 1.

9. The fluorine-containing copolymer according to claim 8, wherein the fluorine-containing polymerizable monomer [VI] is copolymerized in a ratio of 30 wt. % or less in the copolymer.

10. The fluorine-containing copolymer according to claim 9, wherein the fluorine-containing polymerizable monomer [VI] is copolymerized in a ratio of 10 to 30 wt. % in the copolymer.

11. The fluorine-containing copolymer according to claim 1, which is used as an active ingredient of a water- and oil-repellent.

12. The fluorine-containing copolymer according to claim 1, which is used as a surface-treatment agent for powder.

* * * * *